US010849689B1

(12) United States Patent
Hu et al.

(10) Patent No.: US 10,849,689 B1
(45) Date of Patent: Dec. 1, 2020

(54) TECHNOLOGIES FOR PREOPERATIVE IMPLANT SIZE ESTIMATION

(71) Applicant: Smith & Nephew, Inc., Memphis, TN (US)

(72) Inventors: Yangqiu Hu, San Antonio, TX (US); Edward Domanski, Cordova, TN (US)

(73) Assignee: Smith & Nephew, Inc., Memphis, TN (US)

( * ) Notice: Subject to any disclaimer, the term of this patent is extended or adjusted under 35 U.S.C. 154(b) by 525 days.

(21) Appl. No.: 15/686,876

(22) Filed: Aug. 25, 2017

Related U.S. Application Data

(60) Provisional application No. 62/380,092, filed on Aug. 26, 2016, provisional application No. 62/530,577, filed on Jul. 10, 2017.

(51) Int. Cl.
| | |
|---|---|
| *A61B 17/58* | (2006.01) |
| *A61B 17/60* | (2006.01) |
| *A61F 2/00* | (2006.01) |
| *A61B 34/10* | (2016.01) |
| *G06N 7/00* | (2006.01) |
| *A61F 2/46* | (2006.01) |
| *A61F 2/38* | (2006.01) |
| *G06N 20/00* | (2019.01) |

(Continued)

(52) U.S. Cl.
CPC .............. *A61B 34/10* (2016.02); *A61F 2/38* (2013.01); *A61F 2/4657* (2013.01); *G06N 7/005* (2013.01); *G06N 20/00* (2019.01); *A61B 2034/108* (2016.02); *A61F 2002/4633* (2013.01); *G16H 40/63* (2018.01); *G16H 50/30* (2018.01); *G16H 50/50* (2018.01)

(58) Field of Classification Search
CPC combination set(s) only.
See application file for complete search history.

(56) References Cited

U.S. PATENT DOCUMENTS

2017/0061375 A1\* 3/2017 Laster ................ G06Q 10/0875

OTHER PUBLICATIONS

Miller AG, Purtill JJ. Accuracy of digital templating in total knee arthroplasty. Am J Orthop (Belle Mead NJ). Nov. 2012;41(11):510-2.

(Continued)

*Primary Examiner* — Sameh R Boles
(74) *Attorney, Agent, or Firm* — Troutman Pepper Hamilton Sanders LLP

(57) ABSTRACT

A computing system according to an embodiment includes at least one processor and at least one memory comprising a plurality of instructions stored thereon that, in response to execution by the at least one processor, causes the computing system to determine a plurality of implant size predictions with associated confidence levels based on one or more patient or surgical parameters, wherein each of the implant size predictions identifies a confidence level that a prospective implant of a corresponding size will fit a patient, determine whether a combined confidence level determined based on a subset of the plurality of associated confidence levels is at least a threshold value, and recommend, in response to a determination that the combined confidence level is not at least the threshold value, incorporation of at least one of an additional implant size prediction of the plurality of implant size predictions in the subset or digital templating data to improve an accuracy of an implant size estimation.

8 Claims, 12 Drawing Sheets

(51) Int. Cl.
G16H 40/63 (2018.01)
G16H 50/30 (2018.01)
G16H 50/50 (2018.01)

(56) References Cited

OTHER PUBLICATIONS

Specht LM, Levitz S, Iorio R, Healy WL, Tilzey JF. A comparison of acetate and digital templating for total knee arthroplasty. Clin Orthop Relat Res. Nov. 2007;464:179-83.

Issa K, Pivec R, Boyd B, Harwin SF, Wuestemann T, Nevelos J, Mont MA. Comparing the accuracy of radiographic preoperative digital templating for a second- versus a first-generation THA stem. Orthopedics. Dec. 2012;35(12):1028-34.

Steinberg EL, Shasha N, Menaham A, Dekel S. Preoperative planning of total hip replacement using the TraumaCad system. Arch Orthop Trauma Surg. Dec. 2010;130(12):1429-32.

* cited by examiner

PREDICTIVE MODELS

- 504 GENDER ◎ FEMALE ◎ MALE
- 506 AGE [61]
- 508 WEIGHT [77] KG OR [ ] LB
- 510 HEIGHT [1.55] METER OR [ ] FOOT [ ] INCH
- 512 IMPLANT ◎ LEGION P/S ◎ LEGION C/R ◎ JOURNEY II BCS ◎ JOURNEY II C/R
- 514 FEM PREF. ◎ DOWNSIZE ◎ UPSIZE UNLESS ML OVERHANG ◎ UPSIZE
- 516 TIB PREF. ◎ DOWNSIZE ◎ BEST FIT ◎ UPSIZE

[PREDICT IMPLANT SIZES]

| SIZE | 1 | 2 | 3 | 4 | 5 | 6 | 7 | 8 | 9 |
|---|---|---|---|---|---|---|---|---|---|
| FEM PREDICTION | | | 20 | 51 | 24 | 5 | | | |
| TIB PREDICTION | 6 | 37 | 40 | 14 | 2 | 1 | | | |

PREDICTED SIZES FEM [4] TIB [3]

DT SIZES FEM [ ] TIB [ ]

[UPLOAD DT SIZES]

FIG. 5

PREDICTIVE MODELS

- 504 GENDER ◉ FEMALE ◉ MALE
- 506 AGE [66]
- 508 WEIGHT [99] KG OR [ ] LB
- 510 HEIGHT [1.75] METER OR [ ] FOOT [ ] INCH
- 512 IMPLANT ◉ LEGION P/S ◉ LEGION C/R ◉ JOURNEY II BCS ◉ JOURNEY II C/R
- 514 FEM PREF. ◉ DOWNSIZE ◉ UPSIZE UNLESS ML OVERHANG ◉ UPSIZE
- 516 TIB PREF. ◉ DOWNSIZE ◉ BEST FIT ◉ UPSIZE

[PREDICT IMPLANT SIZES]

| SIZE | 1 | 2 | 3 | 4 | 5 | 6 | 7 | 8 | 9 |
|---|---|---|---|---|---|---|---|---|---|
| FEM PREDICTION | | | | 2 | 14 | 42 | 29 | 12 | 1 |
| TIB PREDICTION | | | | 4 | 24 | 44 | 20 | 6 | 2 |

PREDICTED SIZES FEM [6] TIB [6]

DT SIZES FEM [ ] TIB [ ]

WARNING: LOW CONFIDENCE PREDICTIONS. PLEASE USE DIGITAL TEMPLATING

[UPLOAD DT SIZES]

FIG. 6

| MODEL | SURGEON 1 | SURGEON 2 | SURGEON 3 | SURGEON 4 | SURGEON 4 | AVERAGE |
|---|---|---|---|---|---|---|
| NUMBER OF CASES | 381 | 352 | 286 | 268 | 232 | 304 |
| FEMUR GENERIC | 95.8% | 93.2% | 96.2% | 94.4% | 93.1% | 94.5% |
| FEMUR SURGEON-SPECIFIC | 96.9% | 93.2% | 96.2% | 95.9% | 97.8% | 96.0% |
| TIBIA GENERIC | 92.1% | 89.5% | 89.5% | 90.7% | 88.4% | 90.0% |
| TIBIA SURGEON-SPECIFIC | 92.9% | 90.3% | 90.9% | 92.5% | 90.1% | 91.4% |
| FEMUR IMPROVEMENT | 1.1% | 0.0% | 0.0% | 1.5% | 4.7% | 1.5% |
| TIBIA IMPROVEMENT | 0.8% | 0.8% | 1.4% | 1.9% | 1.7% | 1.3% |
| AVERAGE IMPROVEMENT | 0.9% | 0.4% | 0.7% | 1.7% | 3.2% | 1.4% |

TECHNOLOGIES FOR PREOPERATIVE IMPLANT SIZE ESTIMATION

CROSS-REFERENCE TO RELATED APPLICATIONS

This application claims the benefit of U.S. Provisional Application Ser. No. 62/380,092 filed on Aug. 26, 2016 and U.S. Provisional Application Ser. No. 62/530,577 filed on Jul. 10, 2017, the contents of each of which are incorporated herein by reference in their entirety.

BACKGROUND

It is important to ensure that a surgical implant is properly sized for a particular patient. Oftentimes, an implant manufacturer supplies a sizing apparatus that a surgeon uses to intraoperatively estimate the appropriate femoral implant size. However, it is often beneficial to preoperatively estimate the size of the components in total knee, hip, and shoulder arthroplasty and other orthopaedic reconstruction surgeries, for example, to reduce costs associated with the manufacturing, packaging, transporting, inventory/storage, and/or sanitation of the many possible sizes of implants that could possibly fit a particular patient. Preoperative estimations also generally serve as a better starting point for surgeons to more efficiently determine an appropriate implant size during a surgery than an arbitrarily selected size. However, in many circumstances, preoperative estimation techniques involve the use of x-rays, which subject the patient to radiation, incur additional costs, and may unnecessarily delay surgery.

SUMMARY

In one embodiment, a computing system may include at least one processor and at least one memory comprising a plurality of instructions stored thereon that, in response to execution by the at least one processor, causes the computing system to determine a plurality of implant size predictions with associated confidence levels based on one or more patient or surgical parameters, determine whether a combined confidence level based on a subset of confidence levels is at least a threshold value, and recommend incorporation of an additional implant size prediction in the subset and/or digital templating data to improve an accuracy of an implant size estimation. Each implant size prediction may identify a confidence level that a prospective implant of a corresponding size will fit a patient. Further embodiments, forms, features, and aspects of the present application shall become apparent from the description and figures provided herewith.

BRIEF DESCRIPTION OF THE DRAWINGS

The concepts described herein are illustrative by way of example and not by way of limitation in the accompanying figures. For simplicity and clarity of illustration, elements illustrated in the figures are not necessarily drawn to scale. Where considered appropriate, references labels have been repeated among the figures to indicate corresponding or analogous elements.

FIGS. 5-6 are simplified diagrams of a graphical user interface that may be displayed by the computing device of FIG. 1;

DETAILED DESCRIPTION OF THE DRAWINGS

Figure 1:
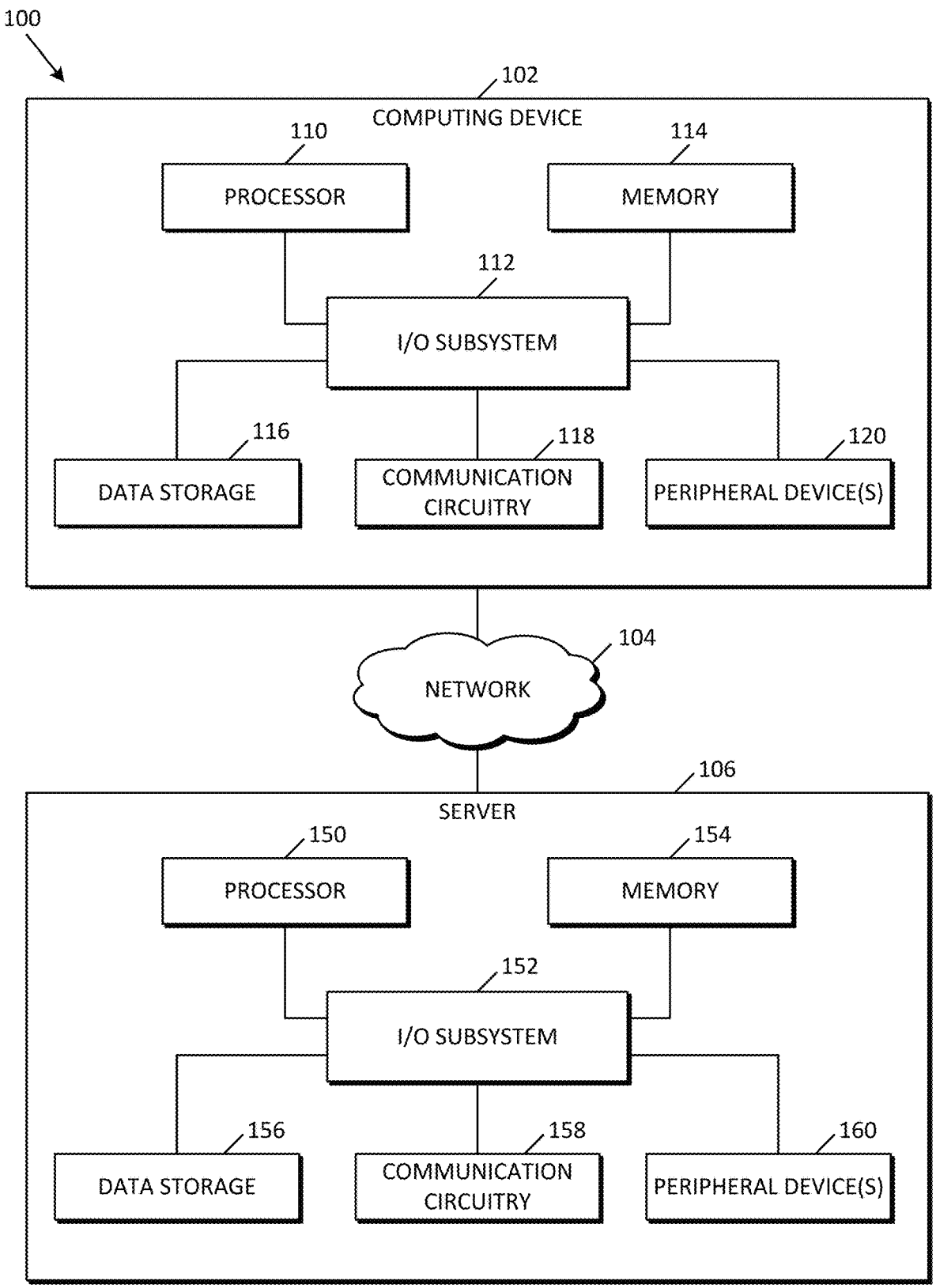
FIG. 1 is a simplified block diagram of a system for preoperative implant size estimation.

Although the concepts of the present disclosure are susceptible to various modifications and alternative forms, specific embodiments have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. It should further be appreciated that although reference to a "preferred" component or feature may indicate the desirability of a particular component or feature with respect to an embodiment, the disclosure is not so limiting with respect to other embodiments, which may omit such a component or feature. Further, when a particular feature, structure, or characteristic is described in connection with an embodiment, it is submitted that it is within the knowledge of one skilled in the art to implement such feature, structure, or characteristic in connection with other embodiments whether or not explicitly described. Additionally, it should be appreciated that items included in a list in the form of "at least one of A, B, and C" can mean (A); (B); (C); (A and B); (B and C); (A and C); or (A, B, and C). Similarly, items listed in the form of "at least one of A, B, or C" can mean (A); (B); (C); (A and B); (B and C); (A and C); or (A, B, and C). Further, with respect to the claims, the use of words and phrases such as "a," "an," "at least one," and/or "at least one portion" should not be interpreted so as to be limiting to only one such element unless specifically stated to the contrary, and the use of phrases such as "at least a portion" and/or "a portion" should be interpreted as encompassing both embodiments including only a portion of such element and embodiments including the entirety of such element unless specifically stated to the contrary.

The disclosed embodiments may, in some cases, be implemented in hardware, firmware, software, or a combination thereof. The disclosed embodiments may also be implemented as instructions carried by or stored on one or more transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, in the illustrative embodiment, an illustrative system 100 for preoperative implant size estimation includes a computing device 102, a network 104, and a server 106. As described in detail below, the system 100 determines a confidence level associated with each of a plurality of implant sizes of a prospective implant based on one or more patient and/or surgical parameters. Further, the system 100 may recognize a particular case as an outlier with low confidence based on the confidence levels and a predefined threshold value corresponding with a desired level of confidence. In such circumstances, the system 100 may alert the user of the low confidence and/or recommend the additional or alternative use of digital templating and/or an additional implant size prediction for verification, for example, before the predicted sizes are used to guide a further logistics workflow associated with the associated surgical procedure and/or preparation.

The computing device 102 may be embodied as any type of computing device capable of performing the functions described herein. For example, the computing device 102 may be embodied as a desktop computer, laptop computer, tablet computer, notebook, netbook, Ultrabook™, cellular phone, smartphone, wearable computing device, personal digital assistant, mobile Internet device, Internet of Things (IoT) device, server, router, switch, and/or any other computing/communication device capable of performing the functions described herein. As shown in FIG. 1, the illustrative computing device 102 includes a processor 110, an input/output ("I/O") subsystem 112, a memory 114, a data storage 116, a communication circuitry 118, and one or more peripheral devices 120. Of course, the computing device 102 may include other or additional components, such as those commonly found in a typical computing device (e.g., various input/output devices and/or other components), in other embodiments. Additionally, in some embodiments, one or more of the illustrative components may be incorporated in, or thereof, may be incorporated in the processor 110 in some embodiments. Although a single computing device 102 is illustratively shown, it should be appreciated that one or more of the components of the computing device 102 described herein may be distributed across multiple computing devices. In other words, the techniques described herein may be employed by a computing system that includes one or more computing devices.

The processor 110 may be embodied as any type of processor capable of performing the functions described herein. For example, the processor 110 may be embodied as a single or multi-core processor(s), digital signal processor, microcontroller, or other processor or processing/controlling circuit. Similarly, the memory 114 may be embodied as any type of volatile or non-volatile memory or data storage capable of performing the functions described herein. In operation, the memory 114 may store various data and software used during operation of the computing device 102 such as operating systems, applications, programs, libraries, and drivers. The memory 114 is communicatively coupled to the processor 110 via the I/O subsystem 112, which may be embodied as circuitry and/or components to facilitate input/output operations with the processor 110, the memory 114, and other components of the computing device 102. For example, the I/O subsystem 112 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 112 may form a portion of a system-on-a-chip (SoC) and be incorporated, along with the processor 110, the memory 114, and other components of the computing device 102, on a single integrated circuit chip.

The data storage 116 may be embodied as any type of device or devices configured for short-term or long-term storage of data such as, for example, memory devices and circuits, memory cards, hard disk drives, solid-state drives, or other data storage devices. The data storage 116 and/or the memory 114 may store various data during operation of the computing device 102 useful for performing the functions described herein.

The communication circuitry 118 may be embodied as any communication circuit, device, or collection thereof, capable of enabling communications between the computing device 102 and other remote devices (e.g., the server 106) over a network (e.g., the network 104). The communication circuitry 118 may be configured to use any one or more communication technologies (e.g., wireless or wired communications) and associated protocols (e.g., Ethernet, Bluetooth®, Wi-Fi®, WiMAX, etc.) to effect such communication.

The peripheral devices 120 may include any number of additional peripheral or interface devices, such as speakers, microphones, additional storage devices, and so forth. The particular devices included in the peripheral devices 120 may depend on, for example, the type and/or intended use of the computing device 102. For example, in some embodiments, the peripheral devices 120 may include a keyboard, mouse, display, touchscreen display, printer, alarm, status indicator, handheld device, diagnostic tool, reader device, and/or one or more other suitable peripheral devices.

The network 104 may be embodied as any type of communication network capable of facilitating communication between the computing device 102 and remote devices (e.g., the server 106). As such, the network 104 may include one or more networks, routers, switches, computers, and/or other intervening devices. For example, the network 104 may be embodied as or otherwise include one or more cellular networks, telephone networks, local or wide area networks, publicly available global networks (e.g., the Internet), ad hoc networks, short-range communication links, or a combination thereof.

The server 106 may be embodied as any type of computing device capable of performing the functions described herein. For example, the server 106 may be embodied as a server, desktop computer, laptop computer, tablet computer, notebook, netbook, Ultrabook™, cellular phone, smartphone, wearable computing device, personal digital assistant, mobile Internet device, Internet of Things (IoT) device, router, switch, and/or any other computing/communication device capable of performing the functions described herein. In some embodiments, the server 106 may be similar to the computing device 102 described above. For example, as shown in FIG. 1, the illustrative server 106 includes a processor 150, an I/O subsystem 152, a memory 154, a data storage 156, a communication circuitry 158, and one or more peripheral devices 160. Those components may be similar to the corresponding components of the computing device 102 described above and, therefore, the descriptions have not been repeated herein for clarity of the description. Further, it should be appreciated that the server 106 may include other components, sub-components, and/or devices commonly found in a computing device, which are not discussed herein for clarity of the description. Additionally, in some embodiments, one or more of the components of the computing device 102 may be omitted from the server 106 (e.g., the peripheral devices 160).

Although only one computing device 102, one network 104, and one server 106 are shown in the illustrative embodiment of FIG. 1, the system 100 may include multiple computing device 102, networks 104, and/or servers 106 in other embodiments. For example, in some embodiments, the computing device 102 may communicate with multiple servers 106. Further, in some embodiments, it should be appreciated that the computing device 102 may perform all of the functions described herein (e.g., the functions of both the computing device 102 and the server 106).

Figure 2:
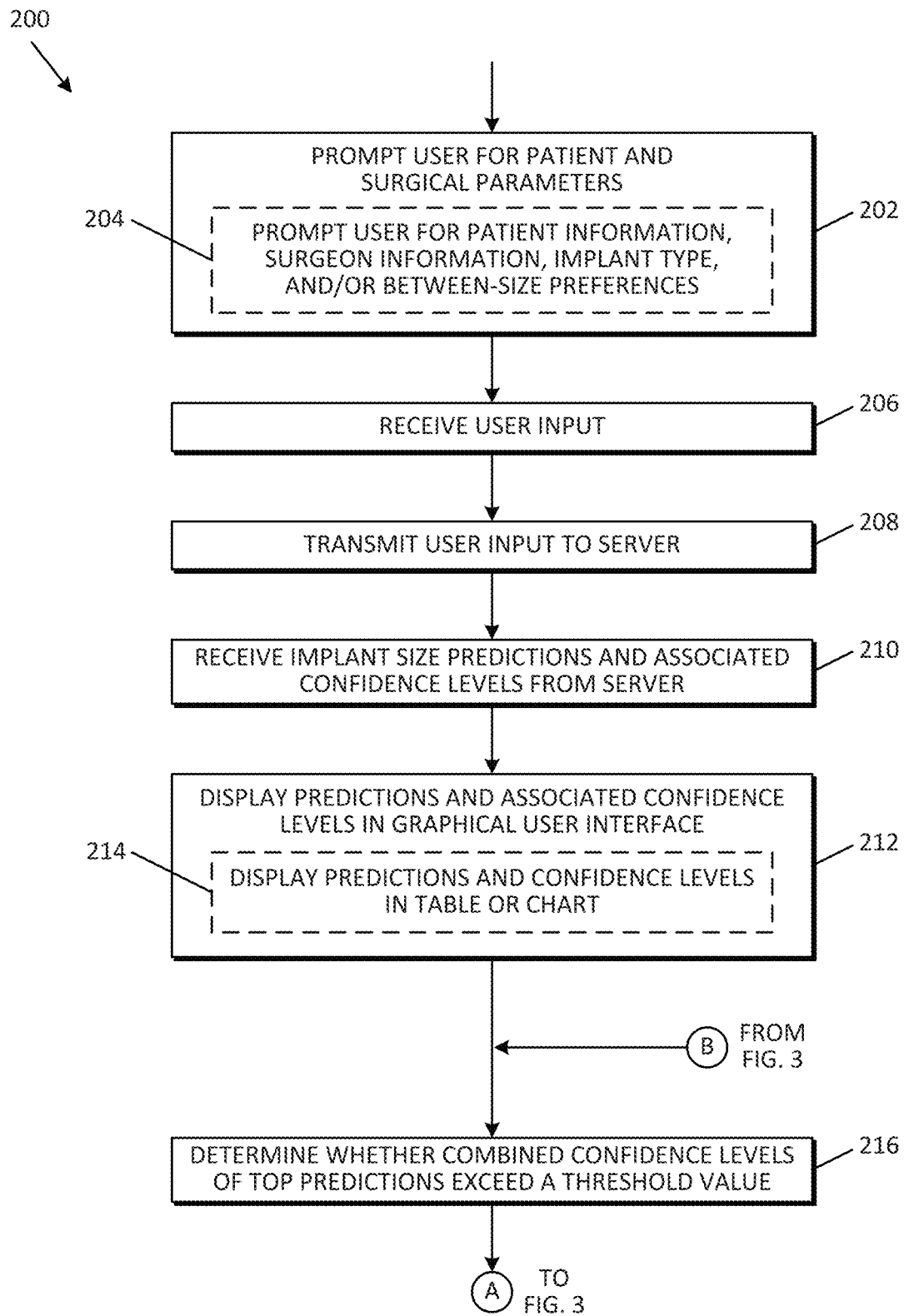
FIGS. 2-3 are a simplified block diagram of at least one embodiment of a method for preoperative implant size estimation that may be executed by a computing device of FIG. 1.
Figure 3:
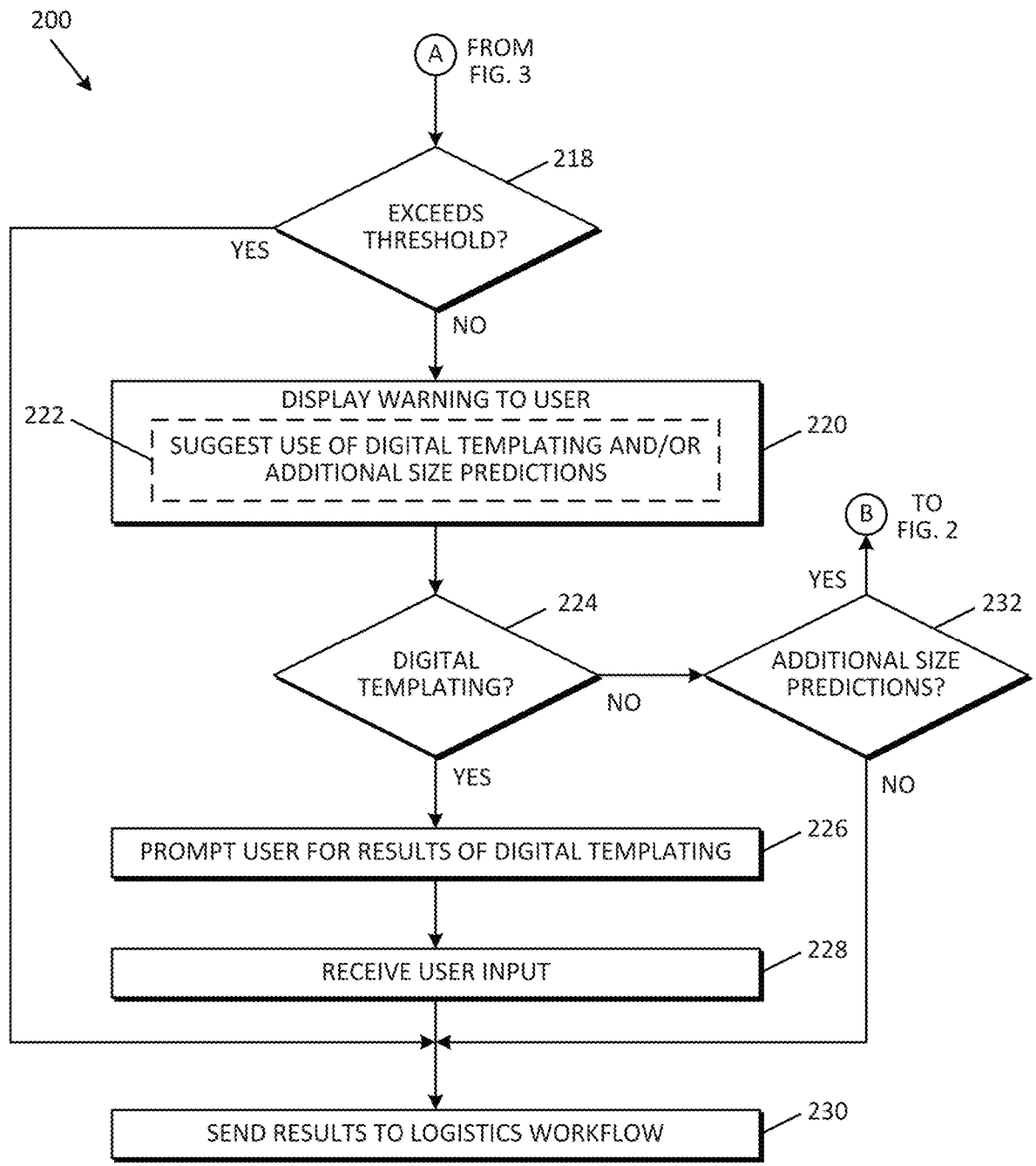

Referring now to FIGS. 2-3, in use, the computing device 102 may execute a method 200 for preoperative implant size estimation. That is, in the illustrative embodiment, the computing device 102 may preoperatively estimate one or more sizes of a prospective implant (e.g., knee implant, hip implant, or shoulder implant) likely to properly fit a patient in a surgical operation. Additionally, in some embodiments, the computing device 102 may preoperatively estimate a set of prospective implants for multiple patients over a period of time (e.g., one surgery day) for high-volume surgeons who operate on many patients and/or high-volume hospitals or surgery centers that may receive implants for multiple planned operations simultaneously (e.g., in a bundle).

It should be appreciated that the particular blocks of the method 200 are illustrated by way of example, and such blocks may be combined or divided, added or removed, and/or reordered in whole or in part depending on the particular embodiment, unless stated to the contrary. The illustrative method 200 begins with block 202 in which the computing device 102 prompts the user for patient and surgical parameters (e.g., via one or more peripheral devices 120). In particular, in block 204, the computing device 102 may prompt the user for patient information, surgeon information (e.g., the surgeon's identity), a prospective/desired implant type for which to size, between-size preferences (e.g., of the surgeon), and/or other relevant patient/surgical parameters (e.g., patient ethnicity, nationality, birthplace, etc.). It should be appreciated that the patient and surgical parameters requested may vary depending on the particular embodiment. For example, in the illustrative embodiment, the computing device 102 prompts the user for an age of the patient, a weight of the patient, a height of the patient, a gender of the patient, an implant type (e.g., model number) of the prospective implant, and a between-size preference of the surgeon as shown by the graphical user interface 500 of FIGS. 5-6. In other embodiments, the computing device 102 may prompt the user for additional and/or alternative anthropometric and/or surgery-related data. Further, in some embodiments, the computing device 102 may not prompt the user but, instead, may receive the patient and/or surgical parameters from another computing device or retrieve the patient and/or surgical parameters from the memory 114 or data storage 116 of the computing device 102.

In block 206, the computing device 102 may receive user input indicative of the one or more patient or surgical parameters (e.g., via one or more peripheral devices 120). In block 208, the computing device 102 transmits the received user input indicative of the patient/surgical parameters to the server 106. As described below, in the illustrative embodiment, the server 106 may execute the method 400 of FIG. 4 to determine a plurality of implant size predictions and associated confidence levels based on the patient/surgical parameters and transmit the results to the computing device 102. In some embodiments, the confidence level may indicate a likelihood that a particular size of the prospective implant is to fit a patient having the specified patient parameters (e.g., for a surgery performed based on further specified surgical parameters). It should be appreciated that the confidence level may be represented as a percent likelihood or in another consistent with the techniques described herein. Accordingly, in block 210, the computing device 102 receives the implant size predictions and associated confidence levels from the server 106. In other embodiments, however, it should be appreciated that the computing device 102 may perform the functions of the server 106. For example, in some embodiments, the computing device 102 may determine the implant size predictions and associated confidence levels itself. As such, depending on the particular embodiment, the computing device 102 may determine the implant size predictions with associated confidence levels based on the patient/surgical parameters with or without the cooperation of the server 106.

In block 212, the computing device 102 displays the implant size predictions and associated confidence levels on a graphical user interface 500 (see, for example, FIGS. 5-6). In doing so, in block 214, the computing device 102 may display the implant size predictions with associated confidence levels in a table 502 or chart depicted in the graphical user interface 500 (see, for example, FIGS. 5-6).

In block 216, the computing device 102 may determine whether a combination of the confidence levels (combined confidence levels) of the top size predictions exceeds a threshold value or is at least the threshold value depending on the particular embodiment. In other words, the computing device 102 determines whether a subset of the confidence levels, in combination, exceeds the threshold value. It should be appreciated that the computing device 102 may determine the combined confidence levels in any way consistent with the techniques described herein. For example, in the illustrative embodiment, the computing device 102 determines whether a sum of the top three confidence levels exceeds (or is at least) the threshold value. In some embodiments, the "top" three confidence levels are identified as the greatest confidence levels (e.g., the greatest percent likelihood of a fit). In other embodiments, the greatest confidence level and the confidence levels associated with the next larger/smaller sizes are identified as the "top" three confidence levels (i.e., the confidence levels associated with the size having the greatest confidence level plus or minus one size). It should further be appreciated that the threshold value may be determined in any suitable manner. In some embodiments, the threshold value may be predefined by the system 100, whereas in other embodiments, the threshold value may be user-specified (e.g., via the graphical user interface 500). In the illustrative embodiment, the threshold value is predefined to be a 90% confidence level. In other embodiments, the threshold value may be selected, for example, to be 95% confidence or another desired level of confidence that one of the top sizes will properly fit the patient. Further, in some embodiments, a fewer or greater number of confidence levels may be used in determining the combined confidence level.

If the computing device 102 determines, in block 218 of FIG. 3, that the combined confidence level exceeds (or is at least) the threshold value, the method 200 advances to block 230 in which the computing device 102 may send the results to a logistics workflow to further guide the surgical procedure and/or preparation. In particular, in some embodiments, the computing device 102 may provide the subset (e.g., top three) of predicted sizes and associated confidence levels to the logistics workflow. In some embodiments, the logistics workflow may include execution of the method 1000 of FIG. 10 as described below. If the computing device 102 determines, in block 218, that the combined confidence level does not exceed (or is not at least) the threshold value, the method 200 advances to block 220 in which the computing device 102 displays a warning to a user of the computing device 102. In doing so, in block 222, the computing device 102 may suggest or recommend the use of digital templating and/or an additional size prediction to improve the confidence in the prediction and/or otherwise improve an accuracy of the implant size estimation. In particular, the computing device 102 may display the warning 602 on a graphical user interface 500 as shown in FIG. 6.

Figure 7:
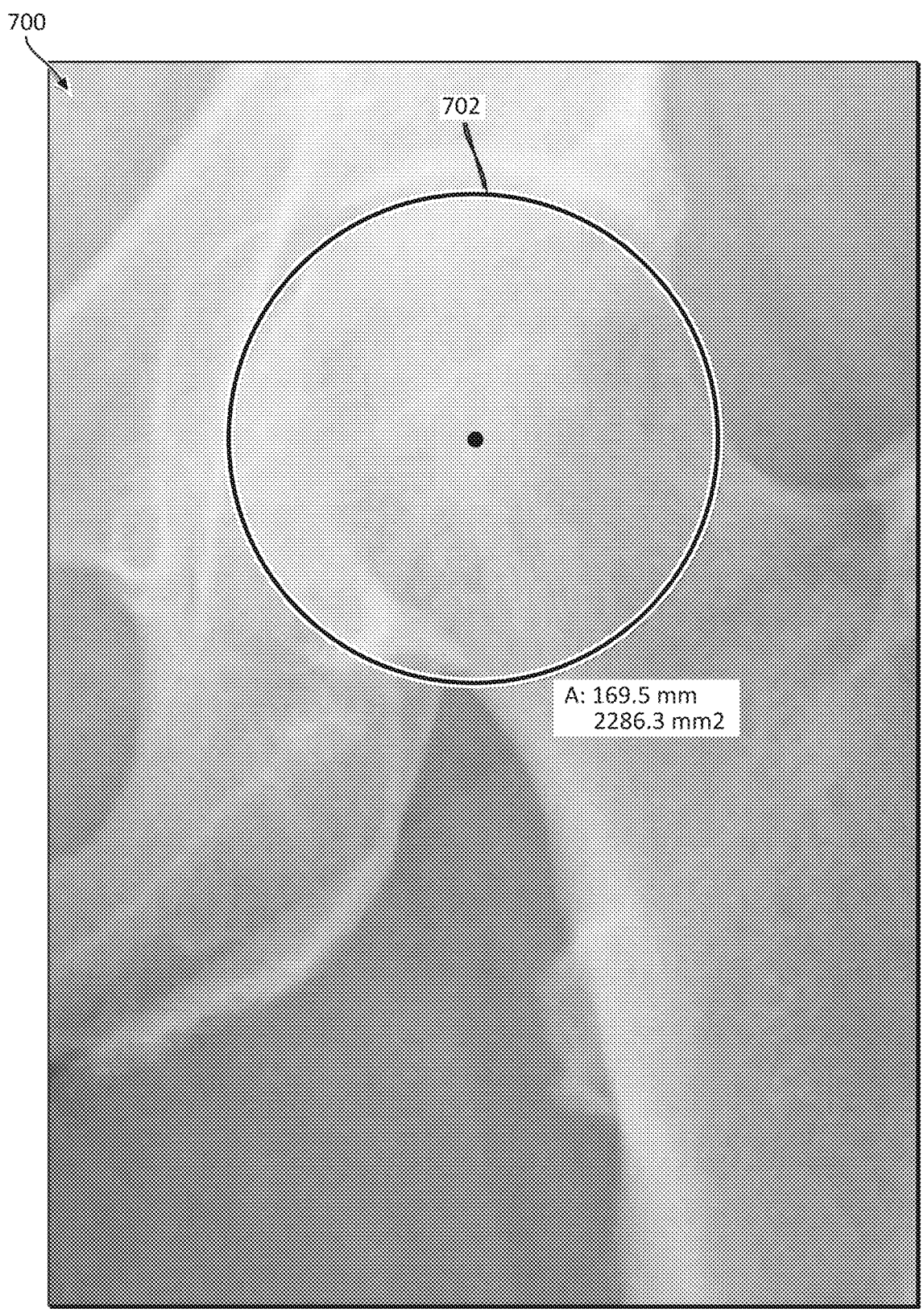
FIG. 7 is an example of an x-ray image that includes a femoral head of a patient's femur.

In block 224, the computing device 102 determines whether to use digital templating to improve the accuracy of the implant size estimation. If so, the method 200 advances to block 226 in which the computing device 102 prompts the user for results of digital templating. For example, in some embodiments, the computing device 102 may prompt the user for the results of the digital templating using the same graphical user interface used to prompt the user for the patient/surgical parameters, to display the implant size predictions and associated confidence levels, and/or another suitable graphical user interface (see, for example, the graphical user interface 500 of FIGS. 5-6). In block 228, the computing device 102 receives user input indicative of the results of the digital templating. In some embodiments, the user input indicative of the digital templating results may be in the form of an appropriate size as determined by a digital templating algorithm (see, for example, the graphical user interface 500). In other embodiments, the user may upload a radiograph or x-ray image 700 as shown in FIG. 7 or another suitable preoperative image or model of the relevant bone(s), which may be analyzed by the computing device 102 to improve the accuracy of the preoperative implant size estimation. By way of example, the x-ray image 700 illustrates a knee joint by which a diameter 702 of a femoral head of the patient's femur may be measured to more accurately determine the proper implant size. In block 230, the computing device 102 sends the results associated with the digital templating procedure (e.g., in association with the previously implant size predictions) to the logistics workflow.

Figure 8:
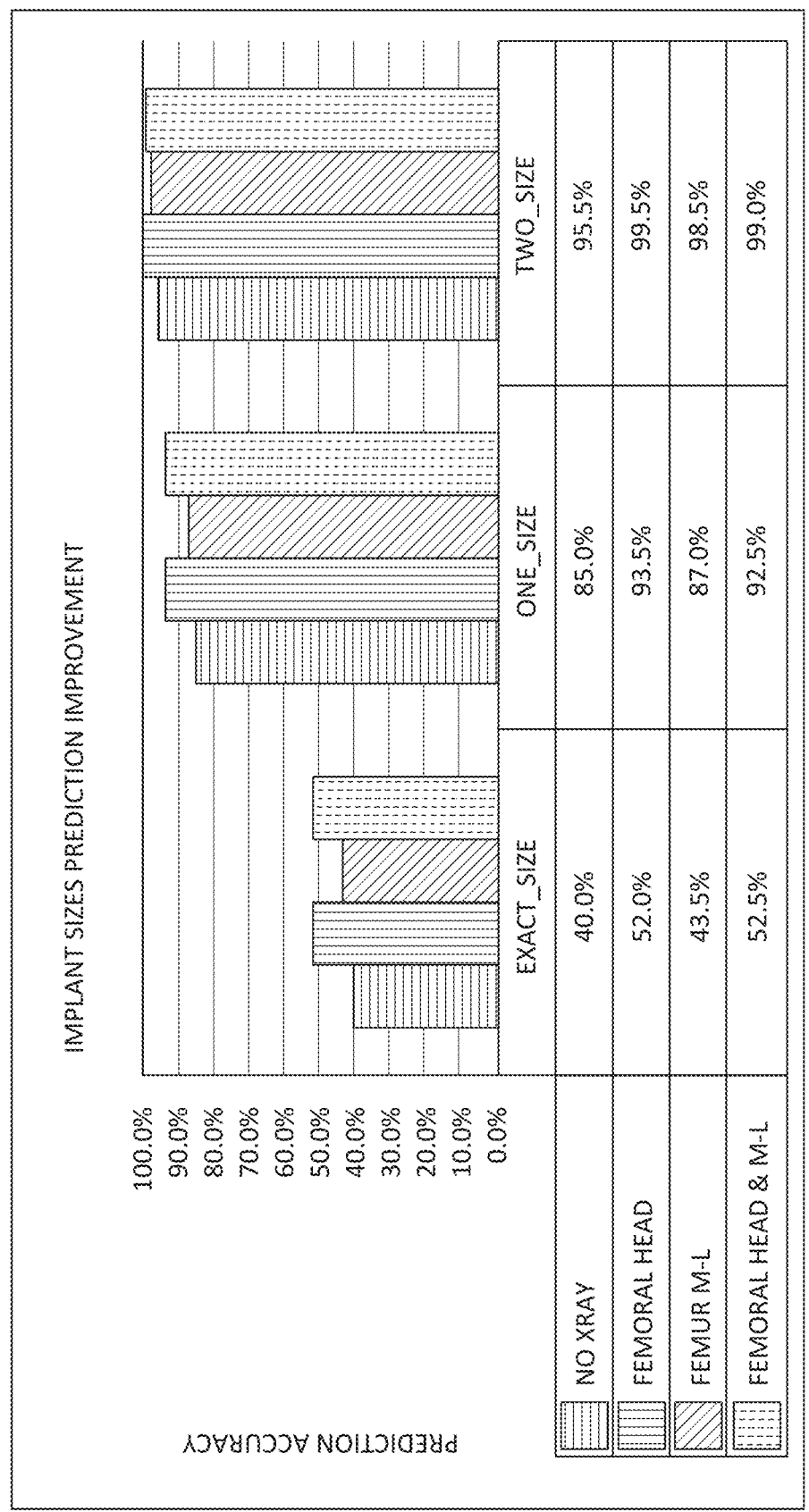
FIG. 8 is a simplified diagram of at least one embodiment of a chart that illustrates an impact of various parameters on an accuracy of an implant size prediction.

As shown in the example table 800 of FIG. 8, the inclusion of measurements taken from an x-ray image or another preoperative image of the patient's bone(s) into the preoperative implant size estimation generally improves the accuracy of the estimation. For example, as shown in the second column of the table 800, the prediction accuracy plus or minus one size may be 85.0% without the incorporation of x-ray image measurements, whereas the prediction accuracy plus or minus one size may be 93.5% with the incorporation of a measurement of a femoral head for a total knee arthroplasty procedure (i.e., an increase of 8.5% prediction accuracy). In other embodiments, other measurements such as a medial-lateral (M-L) measurement of a patient's femur may be incorporated by virtue of digital templating procedures. Although the use of digital templating may, and often does, result in an improved accuracy of the preoperative implant size estimation, digital templating has some significant drawbacks. For example, the use of one or more x-ray images, magnetic resonance images ("MRI"), and/or computer tomography ("CT") images incurs additional cost and may delay the procedure. Further, x-ray images have inherent risks associated with exposing the patient to radiation and oftentimes have perspective projection distortion. As such, it should be appreciated that the techniques described herein achieve a balance by omitting digital templating from the procedure when such imaging is unnecessary to achieve an acceptable confidence level in the preoperative implant size estimation.

Referring back to FIG. 3, if the computing device 102 determines in block 224 not to use digital templating, the computing device 102 determines whether to incorporate one or more additional size predictions into the prediction (e.g., into combined confidence level). For example, the computing device 102 may determine to combine four confidence levels in determining the combined confidence level instead of three confidence levels in an attempt to increase the likelihood that the ideal implant size of the prospective implant is one of the identified/selected sizes. If the computing device 102 determines to incorporate the additional size prediction(s), the method 200 returns to block 216 of FIG. 2 in which the computing device 102 again determines the combined confidence level (i.e., further incorporating the additional size prediction(s)) and proceeds as described above. However, if the computing device 102 determines not to incorporate the additional size prediction(s), the method 200 advances to block 230 in which the computing device 102 sends the results from block 216 to the logistics workflow. In other words, the user and/or the computing device 102 may determine whether to use digital templating and/or an additional size prediction or to proceed without such additional data. Although the blocks 202-230 are described in a relatively serial manner, it should be appreciated that various blocks of the method 200 may be performed in parallel in some embodiments.

Figure 4:
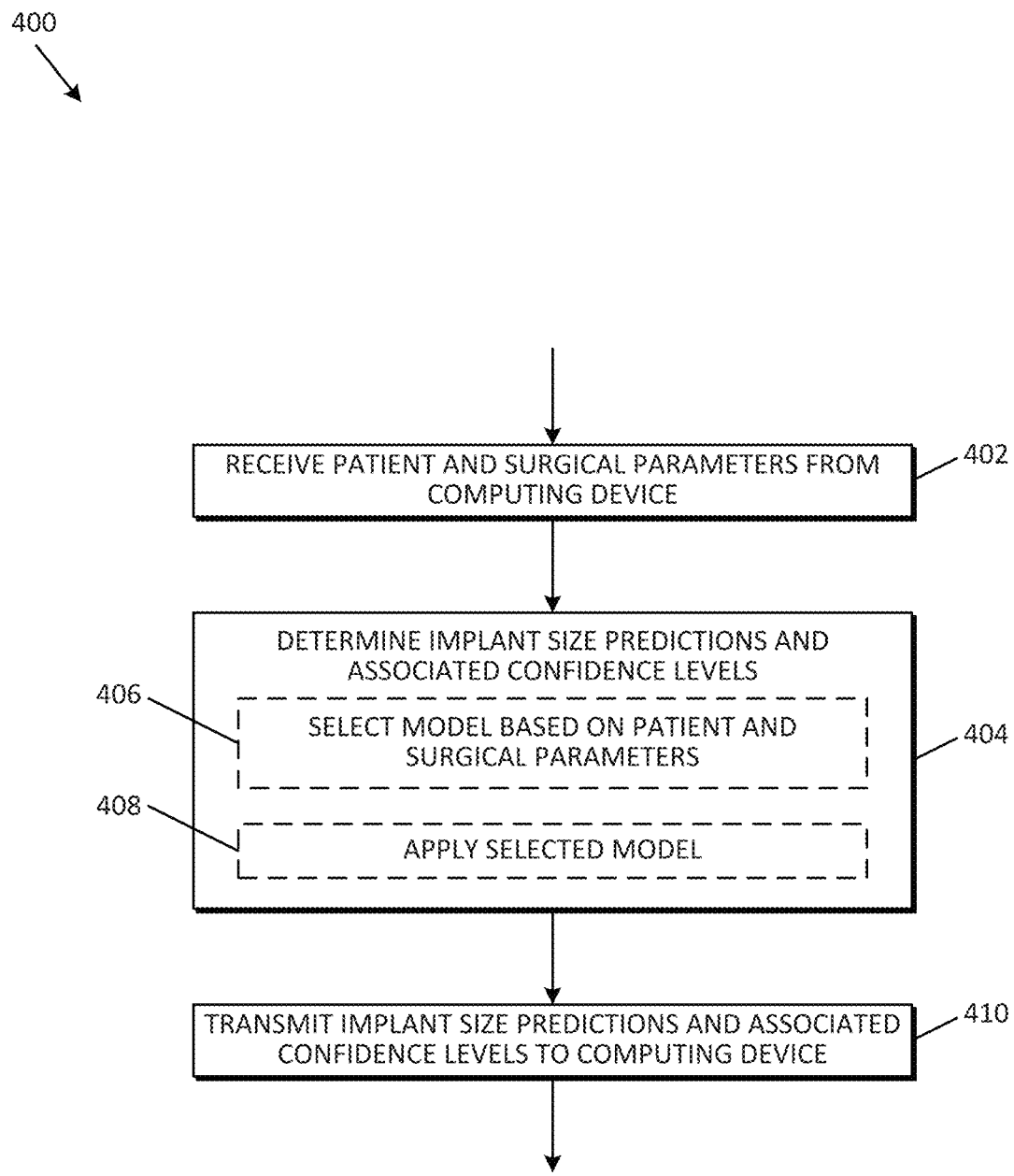
FIG. 4 is a simplified block diagram of at least one embodiment of a method for preoperative implant size estimation that may be executed by a server of FIG. 1.

Referring now to FIG. 4, in use, the server 106 may execute a method 400 for preoperative implant size estimation. It should be appreciated that the particular blocks of the method 400 are illustrated by way of example, and such blocks may be combined or divided, added or removed, and/or reordered in whole or in part depending on the particular embodiment, unless stated to the contrary. As described above, the server 106 may determine a plurality of implant size predictions and associated confidence levels based on the patient/surgical parameters. In particular, the illustrative method 400 begins with block 402 in which the server 106 receive the patient and surgical parameters from the computing device 102 (see, for example, block 208 of FIG. 2).

In block 404, the server 106 determines the implant size predictions and associated confidence levels based on the patient and surgical parameters. For example, in block 406, the server 106 may select a model based on the patient and surgical parameters and, in block 408, the server 108 may apply the selected model to the patient and surgical parameters to determine the confidence levels associated with the relevant implant sizes for a particular prospective implant. It should be appreciated that the model may be any model suitable for determining a confidence level (e.g., percent likelihood of accuracy) of a particular implant size based on the patient and/or surgical parameters. For example, in some embodiments, the server 106 may utilize separate models for male and female patients and separately model various bones. Further, in some embodiments, the model may be embodied as a linear multivariate model that associates anthropometric and/or other parameters (e.g., age, weight, and height) with implant size. More specifically, in some embodiments, a gender-specific model may be used to determine the percent likelihood that a patient of a particular gender, age, weight, and height will fit various implant sizes of a prospective implant type.

It should be appreciated that, in some embodiments, the system 100 may leverage a surgeon-specific predictive model of a particular surgeon (e.g., the surgeon identified in the patient and surgical parameters) for implant size prediction. Such an approach may be particularly beneficial for high-volume surgeons with a sufficiently large number of surgical procedures that his or her surgical predilections may be ascertained. That is, generic or "average" models are typically generated based on an analysis of surgical procedures prepared by many different surgeons (e.g., thousands of procedures by thousands of surgeons) who may have very different surgical approaches and preferences, and who may practice in different regions of the world with different patient demographics and anthropometrics, whereas surgeon-specific models may be "tailored" specifically to that surgeon and his or her patient population.

In some embodiments, surgeons may be divided into three basic tiers based on their case volume: Tier 1 surgeons who typically have sufficient surgical procedures to develop a surgeon-specific model, Tier 2 surgeons who typically do not have sufficient surgical procedures to develop a surgeon-specific model but may be able to tune model parameters to better fit their surgical outcomes, and Tier 3 surgeons who have so few surgical procedures that they should/must rely on a generic model. In some embodiments, the surgeon-specific model may be initially generated and/or updated based on a machine learning algorithm. For example, in some embodiments, a neural network may be employed that is trained to learn, for example, different patterns or signatures associated with sizing and implant prediction, which may be used to generate and/or update the surgeon-specific model.

Figure 11:
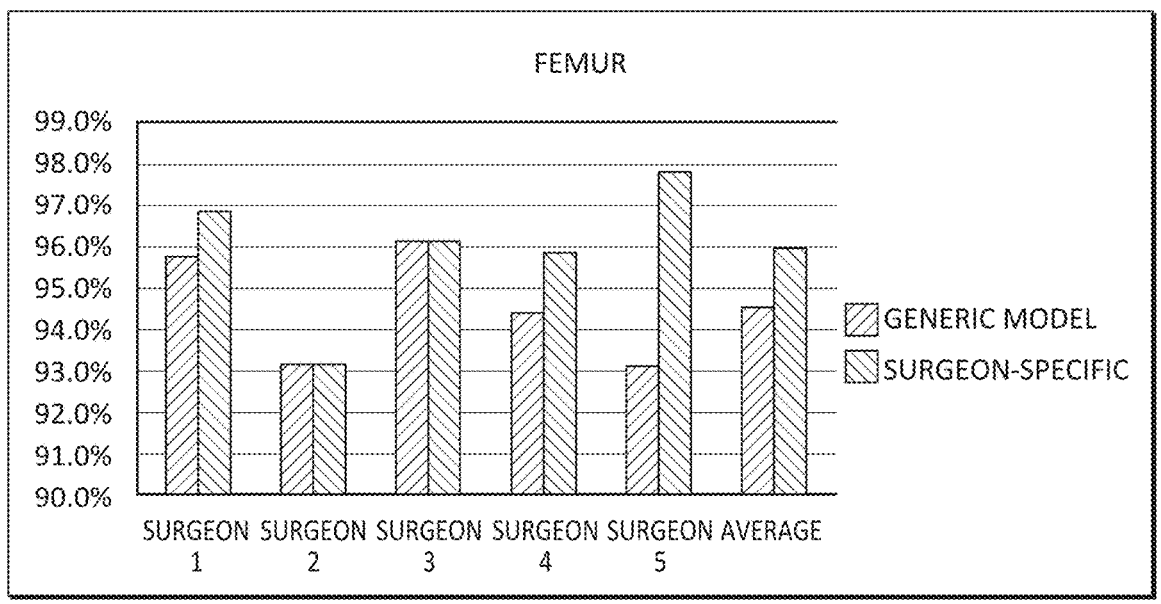
FIG. 11 is a simplified diagram of at least one embodiment of a chart that illustrates a difference in femoral implant size prediction accuracy between the use of a generic model and a surgeon-specific model.
Figure 12:
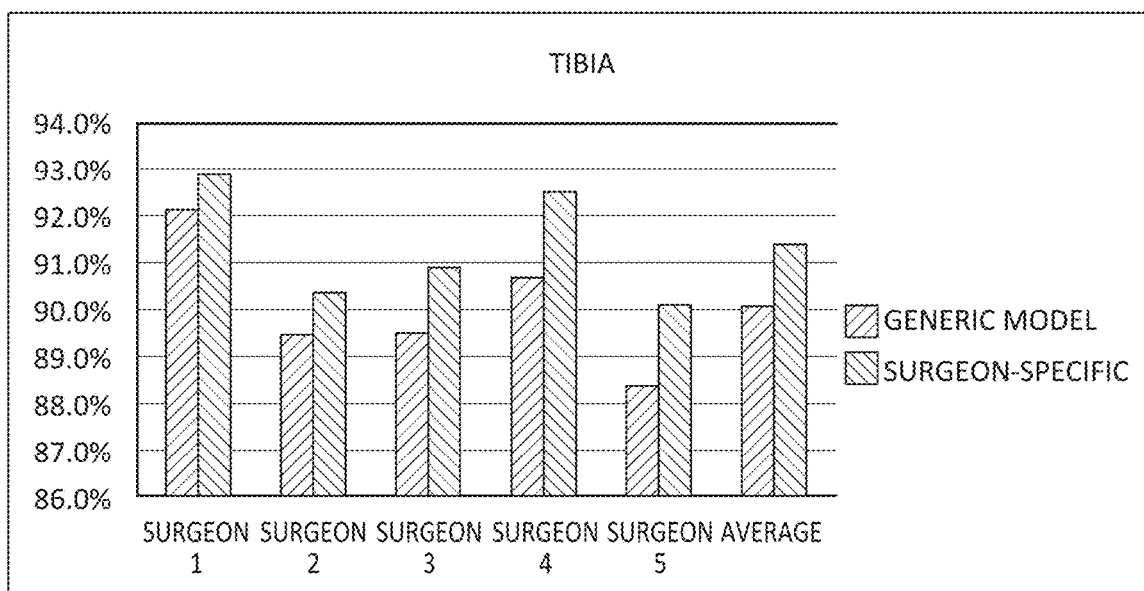
FIG. 12 is a simplified diagram of at least one embodiment of a chart that illustrates a difference in tibial implant size prediction accuracy between the use of a generic model and a surgeon-specific model.
Figures 13, 14:
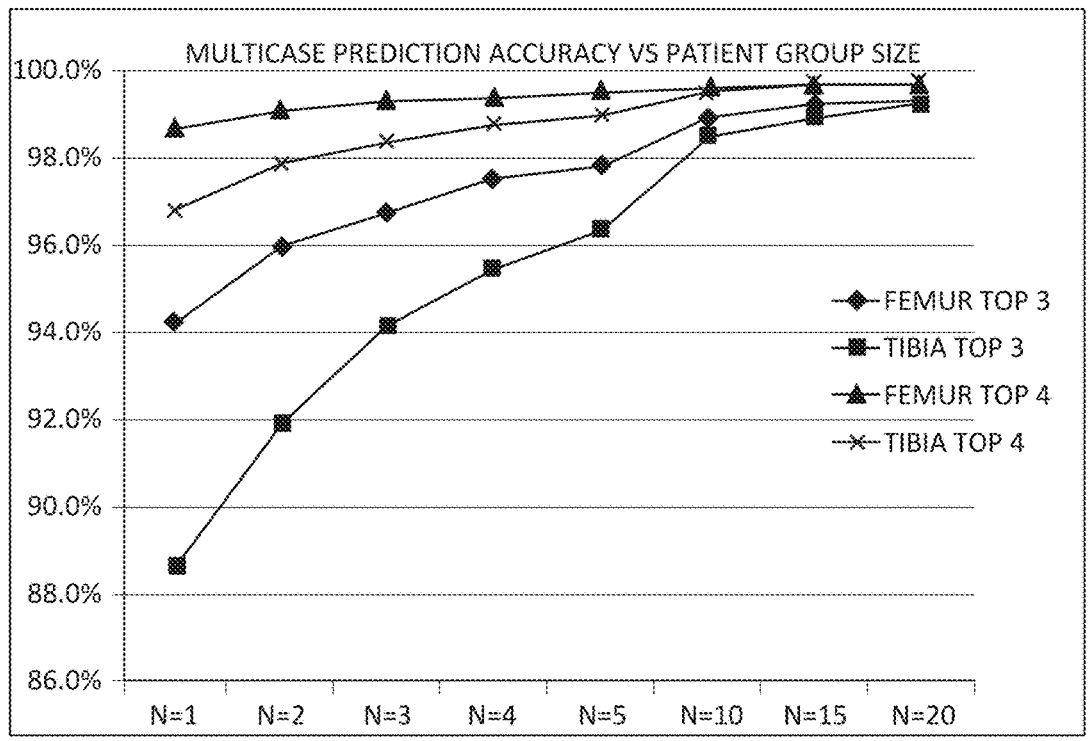
FIG. 13 is a simplified diagram of at least one embodiment of a table that illustrates a difference in implant size prediction accuracy between the use of a generic model and a surgeon-specific model for five different surgeons.
FIG. 14 is a simplified diagram of at least one embodiment of a graph that illustrates a relationship between prediction accuracy and the number of surgical procedures for which implants are received.

As shown in the example chart 1100 of FIG. 11, the use of a surgeon-specific model for a high-volume surgeon (e.g., a Tier 1 surgeon) generally improves the prediction accuracy of a properly sized femoral implant relative to the use of a generic model. Similarly, as shown in the example chart 1200 of FIG. 12, the use of a surgeon-specific model for a high-volume surgeon also generally improves the prediction accuracy of a properly sized tibial implant relative to the use of a generic model. More specifically, the table 1300 of FIG. 13 compares the difference in implant size prediction accuracy between the use of a generic model and a surgeon-specific model for five different Tier 1 surgeons based on a sample data set. The illustrative sample data set was compiled by selecting the top five surgeons by volume of surgical procedures in an anonymized data collection and retroactively generating a surgeon-specific model for each of those five surgeons based only on his or her surgical procedures (i.e., omitting the surgical procedures of other surgeons from the model calculus). The prediction accuracy was then computed based on the surgeon-specific models and compared with the prediction accuracy based on the generic model. It should be appreciated that the "top three sizes" prediction accuracy as described above improved by 1.4% (1.5% for femoral implant size prediction accuracy and 1.3% for tibial implant size prediction accuracy) relative to prediction accuracy based on a generic model.

In block 410, the server 106 transmits the implant size predictions and associated confidence levels to the computing device 102 (see, for example, block 210 of FIG. 2). As described above, it should be appreciated that, in some embodiments, the computing device 102 may perform the functions described in reference to the method 400 without the interaction of the server 106.

Referring now to FIGS. 5-6, as indicated above, the computing device 102 may utilize a graphical user interface 500 to convey information to the user, prompt the user for input, and/or to receive user input. As shown, the graphical user interface 500 identifies numerous categories of patient and surgical parameters and prompts the user for associated input and selections. In particular, the graphical user interface 500 requests input associated with a gender 504 of the patient, an age 506 of the patient, a weight 508 of the patient (metric or imperial), a height 510 of the patient (metric or imperial), and an implant type. It should be appreciated that the illustrative graphical user interface 500 is associated with a total knee arthroplasty and, therefore, includes information associated with such a surgical procedure in particular. For example, the specific implant types 512 identified are "Legion P/S," "Legion C/R," "Journey II BCS," and "Journey II C/R." Further, the graphical user interface 500 identifies femoral between-size preferences 514 and tibial between-size preferences 516. In some embodiments, it should be appreciated that the graphical user interface 500 may also prompt the user for input associated with the type of model to be used. In the case of a surgeon-specific model, the graphical user interface 500 may further prompt the user for input associated with the surgeon's identity (e.g., the surgeon's name, DEA number, National Provider Identifier Standard (NPI) number, medical license number, employee identifier, etc.).

In the illustrative example of FIG. 5, the user provided the patient's gender to be female, the patient's age to be 61 years, the patient's weight to be 77 kilograms, and the patient's height to be 1.55 meters and further indicated that the implant size predictions for the corresponding femoral and tibial implants should be determined for the "Legion P/S" implant type with an upsize preference for both the femoral and tibial implants. As shown, the predicted femoral implant size 518 and the predicted tibial implant size 520 are size 4 and size 3, respectively. Further, as shown in the table 502, which depicts the confidence levels corresponding with the various implant sizes determined based on the patient/ surgical parameters, those implant size predictions have relatively high confidence levels. In particular, the femoral implant size prediction of size 4 has a confidence level of 95% for a plus/minus one size prediction (20+51+24=95), and the tibial implant size prediction of size 3 has a confidence level of 91% for a plus/minus one size prediction (37+40+14=91). In the embodiment of FIG. 5, the threshold was established at 90%. Because each of the combined confidence levels exceeds the threshold, the computing device 102 proceeds with the logistics workflow without using digital templating or additional size predictions.

In the illustrative example of FIG. 6, the user provided the patient's gender to be male, the patient's age to be 66 years, the patient's weight to be 99 kilograms, and the patient's height to be 1.75 meters and further indicated that the implant size predictions for the corresponding femoral and tibial implants should be determined for the "Legion P/S" implant type with a downsize preference for the femoral implant and a best fit preference for the tibial implant. As shown, the predicted femoral implant size 518 and the predicted tibial implant size 520 are both size 6. As shown in the table 502 of FIG. 6, the combined confidence levels are relatively low. In particular, the femoral implant size prediction of size 6 has a combined confidence level of 85% (14+42+29=85), and the tibial implant size prediction of size 6 has a confidence level of 88% (24+44+20=88), which are both below the established threshold of 90%. Accordingly, in the illustrative embodiment, the graphical user interface 500 issues a warning message 602 to the user and recommends that the user incorporate digital templating into the preoperative implant size estimation. Accordingly, in the illustrative embodiment, the user may provide the implant sizes determined from the digital templating procedures, i.e., the DT femoral implant size 604 and the DT tibial implant size 606 for further analysis as described above. As such, the computing device 102 may modify the preoperative implant size predictions based further on the digital templating results and provide the modified predictions to the user.

Figure 9:
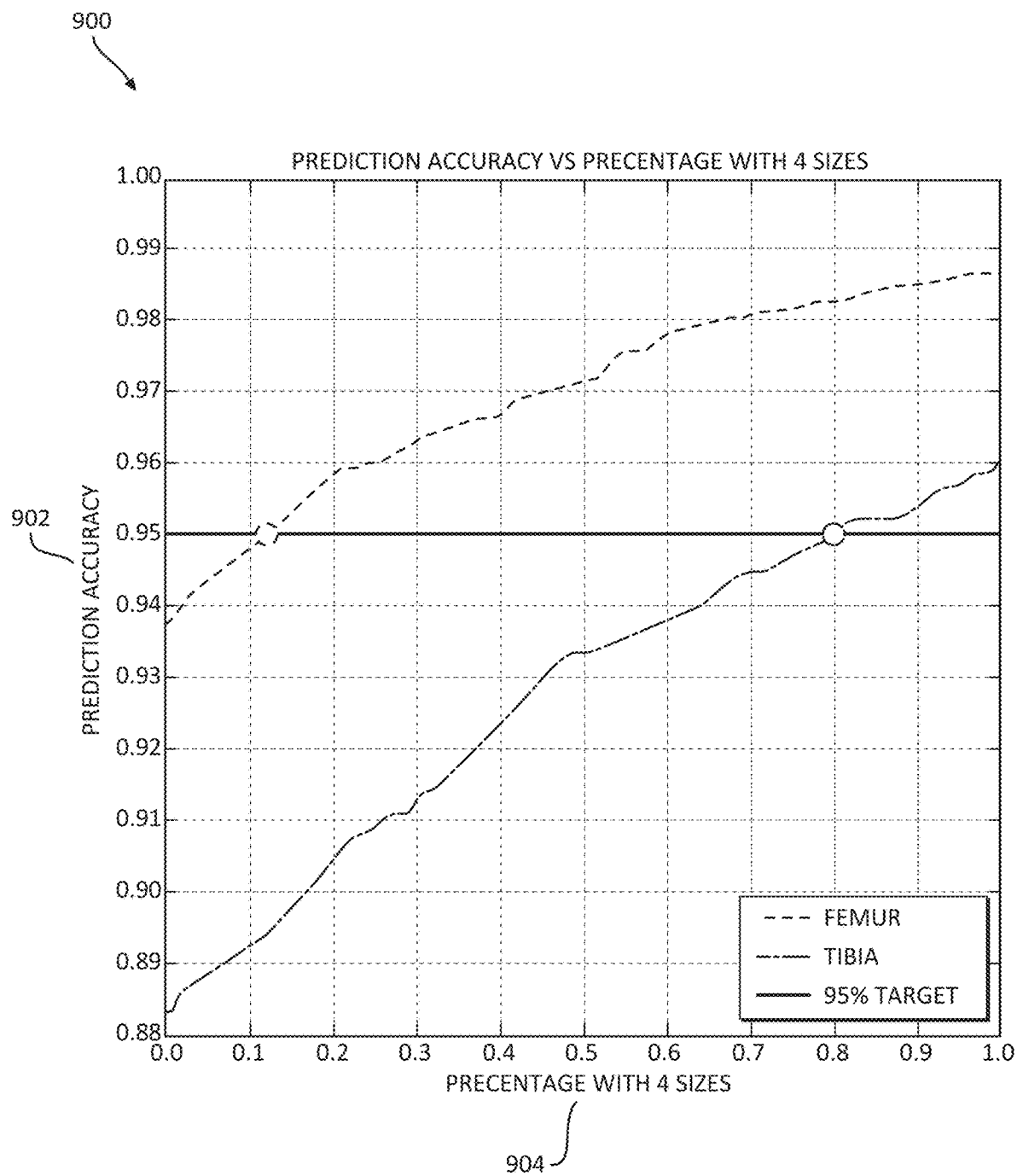
FIG. 9 is a simplified diagram of at least one embodiment of a graph that illustrates a relationship between prediction accuracy and consideration of an additional implant size.

In other embodiments, it should be appreciated that the computing device 102 may additionally, or alternatively, utilize additional size predictions to modify the implant size predictions as described above. By doing so, the computing device 102 may further reduce the need to increase costs associated with digital templating and/or unnecessarily expose the patient to radiation. Referring now to FIG. 9, a graph 900 that illustrates a sample relationship between a prediction accuracy 902 and a percentage 904 of cases with 4 sizes instead of 3 sizes is shown. As shown, based on a sample of certain cases, without the inclusion of digital templating techniques, 12% of femoral implant predictions and 80% of tibial implant predictions may require the use of 4 sizes instead of 3 sizes to ensure that the overall accuracy would be no less than a 95% threshold target. It should be appreciated that a lower threshold (e.g., 90%) would result in even fewer implant predictions requiring a fourth size prediction.

It should be appreciated that, as a practical matter, implants for multiple patients are often shipped (e.g., as a bundle) to a particular hospital or surgical center and are also often stored together. As described above, in many circumstances, several implants of different sizes (e.g., the top three implant size predictions) are shipped in preparation for the surgery. Given that only one surgical implant of those shipped for the particular patient is used in a given operation (e.g., absent contamination or uncommon/unforeseen circumstances), the other shipped implants remain unused and are generally returned or stored for subsequent use. As such, the unused implant sizes are candidates to be used for other surgical procedures as additional available implants, for example, to further reduce the probability of inaccurate implant size prediction. That is, the local storage of the hospital or surgical center may essentially serve as a temporary pool for multiple patients to "share" implant size predictions among one another. As shown in the example graph 1400 of FIG. 14, the logistical efficiency at 95% accuracy can be increased by 25% if the patient group consists of four or more surgical procedures while using three instead of four sizes, and the prediction can achieve an accuracy above 99% with four sizes if the patient group consists of five or more surgical procedures. It should be appreciated that the surgical procedures may be performed by the same surgeon or different surgeons depending on the particular embodiment.

Figure 10:
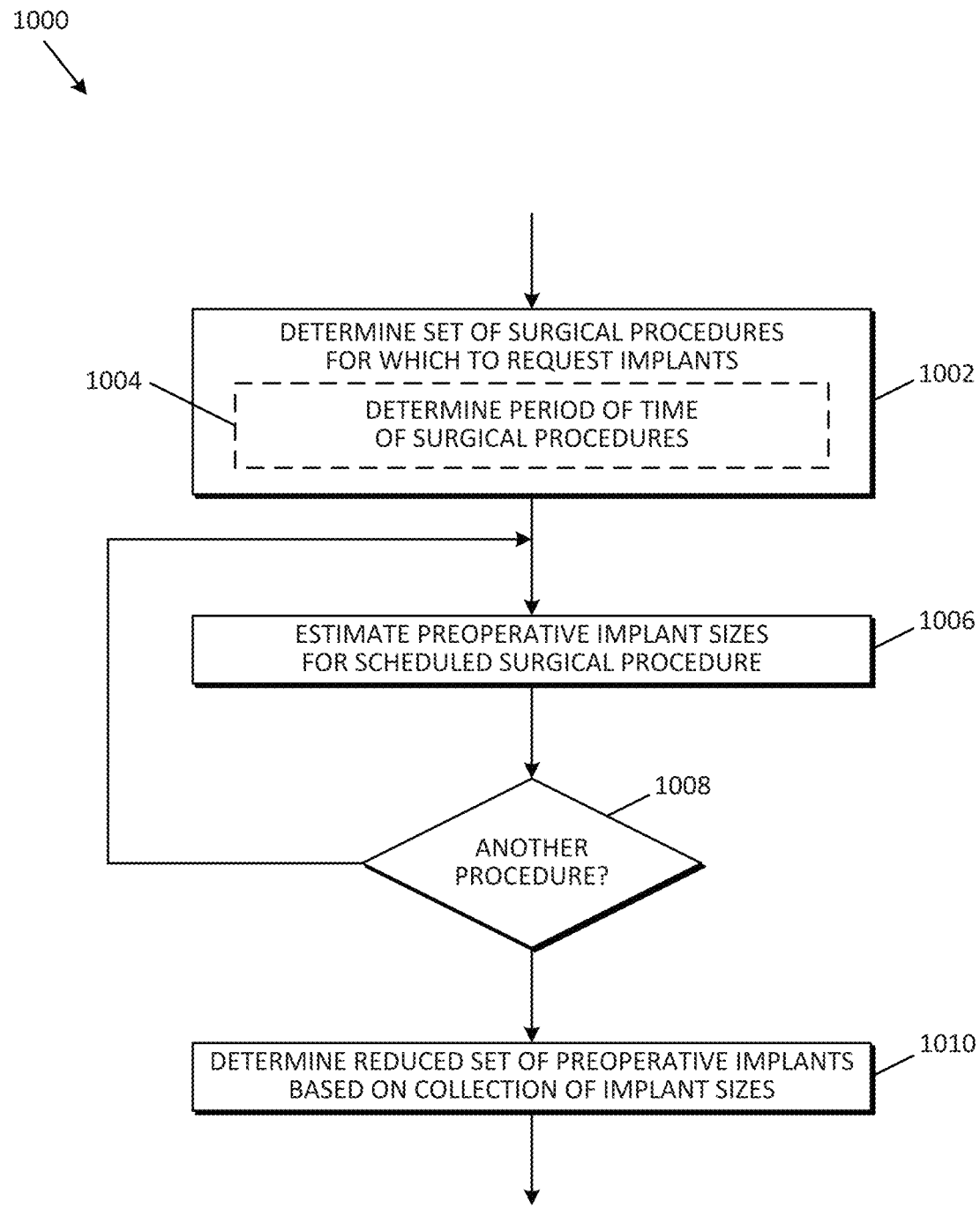
FIG. 10 is a simplified block diagram of at least one embodiment of a method for preoperatively determining a reduced set of implants.

Referring now to FIG. 10, the system 100 or, more specifically, the computing device 102 may execute a method 1000 for preoperatively determining a reduced set of implants required. It should be appreciated that the particular blocks of the method 1000 are illustrated by way of example, and such blocks may be combined or divided, added or removed, and/or reordered in whole or in part depending on the particular embodiment, unless stated to the contrary. The illustrative method 1000 begins with block 1002 in which the computing device 102 determines the set of surgical procedures for which to request implants. In doing so, in block 1004, the computing device 102 may determine a period of time (e.g., a particular surgical day, a week of surgical procedures, etc.) for which implants for the corresponding surgical procedures are to be requested. In other words, the computing device 102 determines which particular surgical procedures should be "bundled" for the purposes of the multi-case prediction described herein. In block 1006, the computing device 102 determines, estimates, and/or retrieves the preoperative implant sizes for a scheduled surgical procedure of the set of surgical procedures identified in block 1002. To do so, in some embodiments, the computing device 102 may execute the method 200 of FIGS. 2-3 or a portion thereof. In particular, in some embodiments, the computing device 102 may receive the results of the analysis of the method 200 as described in reference to block 230 of FIG. 3 (e.g., the subset (e.g., top three) of predicted sizes and associated confidence levels). In block 1008, the computing device 102 determines whether to determine, estimate, and/or retrieve the preoperative implant size(s) for another surgical procedure of the set of surgical procedures for which to request implants. If so, the method 1000 returns to block 1006. In other words, the computing device 102 determines the predicted implant sizes and/or other suitable data for each of the surgical procedures in the set of surgical procedures (e.g., for each of the procedures in a given surgical day).

In block 1010, the computing device 102 determines a reduced set of preoperative implants required based on the collection of implant sizes identified in blocks 1002-1008. For example, a particular surgical day may include five surgical procedures, each of which may be associated with three implant size predictions as described above (i.e., fifteen total implants). Given that the total number of implant sizes is finite, it should be appreciated that there may be some overlap among implant sizes. In such an embodiment, the computing device 102 may identify a reduced set of implants (e.g., to request from a vendor) based on a suitable model and/or algorithm. For example, the computing device 102 may determine that it is only necessary to "bundle" twelve implants for the five surgical procedures instead of fifteen implants.

It should be appreciated that the computing device 102 may utilize any suitable model and/or algorithm for determining the reduce set of implants required for the determined set of surgical procedures. For example, in some embodiments, the computing device 102 may employ a machine learning algorithm. More specifically, in some embodiments, the computing device 102 may utilize a neural network that is trained to learn, for example, different patterns or signatures associated with sizing and implant prediction. For example, the machine learning algorithm may predict that downsizing is more likely than upsizing and make the determinations described above accordingly. In some embodiments, in addition to using a fixed number of sizes (e.g., three or four) for each surgical procedure, the optimal allocation may be estimated using combinatorial optimization with probabilities associated with each predicted size in which case the probability that each size has sufficient number of implants may be calculated.

Although the method 1000 is described above as being executed by the computing device 102 in the illustrative embodiment, it should be appreciated that the method 1000 may be executed by the server 106 or may be executed in conjunction with the server 106 in other embodiments. Additionally, although the blocks 1002-1010 are described in a relatively serial manner, it should be appreciated that various blocks of the method 1000 may be performed in parallel in some embodiments.

The graph 1400 of FIG. 14 illustrates an increase in multi-case prediction accuracy as the number of surgical procedures in a group increases. As indicated above, in some embodiments, the computing device 102 may adopt an approach by which the computing device 102 uses three sizes if there are four patients or more in the group to achieve a prediction accuracy above 95%, and by which the computing device 102 uses four sizes if there are five patients or more in the group to achieve a prediction accuracy above 99%. It should be appreciated that, in order to arrive at the numbers described herein, the multi-case prediction accuracy was analyzed based on a five step approach. First, the surgical procedures were divided into groups with an equal number, N, of surgical procedures. Second, for each group, a counter was maintained for each size to record the number of times that size is included as a "top three" predicted size. Third, all surgical procedures in each group are looped through to compare the actual sizes with the counters for these sizes. If the counter is greater than zero, that is indicative of an implant for the surgical procedure (a hit). If the counter is zero, that is indicative of no implant for the surgical procedure (a miss). Fourth, the total number of "hits" across all groups/procedures was divided by the total number of cases to compute the prediction accuracy. Finally, each of the first four steps were repeated for different numbers, N, of surgical procedures in a group.

In an embodiment, a computing system includes at least one processor and at least one memory comprising a plurality of instructions stored thereon that, in response to execution by the at least one processor, causes the computing system to determine a plurality of implant size predictions with associated confidence levels based on one or more patient or surgical parameters, wherein each of the implant size predictions identifies a confidence level that a prospective implant of a corresponding size will fit a patient, determine whether a combined confidence level determined based on a subset of the plurality of associated confidence levels is at least a threshold value, and recommend, in response to a determination that the combined confidence level is not at least the threshold value, incorporation of at least one of an additional implant size prediction of the plurality of implant size predictions in the subset or digital templating data to improve an accuracy of an implant size estimation.

In some embodiments, the computing system includes a computing device and a server, wherein to determine the plurality of size predictions with associated confidence levels comprises to transmit the one or more patient or surgical parameters from the computing device to the server and receive the plurality of implant size predictions with associated confidence levels from by the computing device and from the server.

In some embodiments, the plurality of instructions further causes the computing system to display the plurality of implant size predictions and associated confidence intervals on a graphical user interface.

In some embodiments, to display the plurality of implant size predictions and associated confidence intervals comprises to display the plurality of implant size predictions and associated confidence intervals in one of a table or a chart of the graphical user interface.

In some embodiments, the plurality of instructions further causes the computing system to prompt a user of the computing system for the one or more patient or surgical parameters and receive user input indicative of the one or more patient or surgical parameters.

In some embodiments, to determine the plurality of implant size predictions with associated confidence levels comprises to select a model based on the one or more patient or surgical parameters and apply the selected model to the one or more patient or surgical parameters to determine the associated confidence levels for the plurality of implant size predictions.

In some embodiments, to select the model includes to select a surgeon-specific model based on a surgeon identified in the one or more patient or surgical parameters.

In some embodiments, the plurality of instructions further causes the computing system to determine the combined confidence level based on the three greatest confidence levels of the associated confidence levels.

In some embodiments, the combined confidence level is a sum of the associated confidence levels in the subset.

In some embodiments, the one or more patient or surgical parameters includes at least one anthropometric measurement of the patient.

In some embodiments, the one or more patient or surgical parameters includes an age of the patient, a weight of the patient, a height of the patient, a gender of the patient, an implant type of the prospective implant, an identity of a surgeon, and a between-size preference.

In some embodiments, the one or more patient and surgical parameters includes a plurality of patient parameters and a plurality of surgical parameters.

In some embodiments, the plurality of instructions further causes the computing system to display a warning on a graphical user interface in response to the determination that the combined confidence level is not at least the threshold value.

In some embodiments, the plurality of instructions further causes the computing system to send results associated with at least one of the combined confidence level or the digital templating to a logistics workflow.

In some embodiments, the logistics workflow includes a determination of a reduced set of implants required based on the results associated with the combined confidence level.

In some embodiments, the plurality of instructions further causes the computing system to determine a set of surgical procedures for which to request implants, and determine a reduced set of implants required based on the determined results associated with the determined set of surgical procedures.

In some embodiments, to determine the set of surgical procedures includes to determine a period of time for which implants for corresponding surgical procedures are to be requested.

In some embodiments, to determine the reduced set of implants required includes to determine the reduced set of implants based on a machine learning algorithm.

In another embodiment, a method for implant size estimation includes determining, by a computing device, a plurality of implant size predictions with associated confidence levels based on one or more patient or surgical parameters, wherein each of the implant size predictions identifies a confidence level that a prospective implant of a corresponding size will fit a patient, determining, by the computing device, whether a combined confidence level determined based on a subset of the plurality of associated confidence levels is at least a threshold value; and recommending, by the computing device and in response to a determination that the combined confidence level is not at least the threshold value, incorporation of at least one of an additional implant size prediction of the plurality of implant size predictions in the subset or digital templating data to improve an accuracy of an implant size estimation.

In some embodiments, the method further includes prompting, by the computing device, a user of the computing device for the one or more patient or surgical parameters; receiving, by the computing device, user input indicative of the one or more patient or surgical parameters; and transmitting, by the computing device, the one or more patient or surgical parameters to a server, wherein determining the plurality of implant size predictions with associated confidence levels comprises receiving, by the computing device and from the server, the plurality of implant size predictions with associated confidence levels.

In some embodiments, to determine the plurality of implant size predictions with associated confidence levels comprises to select a model based on the one or more patient or surgical parameters and apply the selected model to the one or more patient or surgical parameters to determine the associated confidence levels for the plurality of implant size predictions.

In some embodiments, the model includes a surgeon-specific model based on a plurality of prior surgical procedures of the surgeon.

In some embodiments, the method further includes determining, by the computing device, the combined confidence level based on the three greatest confidence levels of the associated confidence levels.

In some embodiments, the method further includes selecting the prospective implant of a desired size based on at least one of the implant size predictions included in the subset and performing a surgical procedure on the patient using the selected prospective implant.

In some embodiments, the method further includes determining a set of surgical procedures for which to request implants, and determining a reduced set of implants required based on the implant size predictions associated with the combined confidence levels of the corresponding surgical procedures.

In some embodiments, determining the reduced set of implants required includes determining the reduced set of implants based on a machine learning algorithm.

In another embodiment, one or more machine-readable storage media comprising a plurality of instructions stored thereon that, in response to execution by a computing device, causes the computing device to determine a plurality of implant size predictions with associated confidence levels based on one or more patient or surgical parameters, wherein each of the implant size predictions identifies a confidence level that a prospective implant of a corresponding size will fit a patient, determine whether a combined confidence level determined based on a subset of the plurality of associated confidence levels is at least a threshold value, and recommend, in response to a determination that the combined confidence level is not at least the threshold value, incorporation of at least one of an additional implant size prediction of the plurality of implant size predictions in the subset or digital templating data to improve an accuracy of an implant size estimation.

In some embodiments, the one or more patient or surgical parameters includes at least one anthropometric measurement of the patient.

What is claimed is:

1. A method for implant size estimation, the method comprising:
    determining, by a computing device, a plurality of implant size predictions with associated confidence levels based on one or more patient or surgical parameters, wherein each of the implant size predictions identifies a confidence level that a prospective implant of a corresponding size will fit a patient;
    determining, by the computing device, whether a combined confidence level determined based on a subset of the plurality of associated confidence levels is at least a threshold value;
    recommending, by the computing device and in response to a determination that the combined confidence level is not at least the threshold value, incorporation of at least one of an additional implant size prediction of the plurality of implant size predictions in the subset or digital templating data to improve an accuracy of an implant size estimation;
    prompting, by the computing device, a user of the computing device for at least one of the additional implant size prediction of the plurality of implant size predictions in the subset or the digital templating data; and
    incorporating, by the computing device, at least one of the additional implant size prediction of the plurality of implant size predictions in the subset or the digital templating data to the patient or surgical parameters.

2. The method of claim 1, further comprising:
    prompting, by the computing device, a user of the computing device for the one or more patient or surgical parameters;
    receiving, by the computing device, user input indicative of the one or more patient or surgical parameters; and
    transmitting, by the computing device, the one or more patient or surgical parameters to a server, wherein determining the plurality of implant size predictions with associated confidence levels comprises receiving, by the computing device and from the server, the plurality of implant size predictions with associated confidence levels.

3. The method of claim 1, wherein to determine the plurality of implant size predictions with associated confidence levels comprises to:

select a model based on the one or more patient or surgical parameters; and apply the selected model to the one or more patient or surgical parameters to determine the associated confidence levels for the plurality of implant size predictions.

4. The method of claim 3, wherein the model comprises a surgeon-specific model based on a plurality of prior surgical procedures of the surgeon.

5. The method of claim 1, further comprising determining, by the computing device, the combined confidence level based on the three greatest confidence levels of the associated confidence levels.

6. The method of claim 1, further comprising:

selecting the prospective implant of a desired size based on at least one of the implant size predictions included in the subset; and performing a surgical procedure on the patient using the selected prospective implant.

7. The method of claim 1, further comprising:

determining a set of surgical procedures for which to request implants; and determining a reduced set of implants required based on the implant size predictions associated with the combined confidence levels of the corresponding surgical procedures.

8. The method of claim 7, wherein determining the reduced set of implants required comprises determining the reduced set of implants based on a machine learning algorithm.

\* \* \* \* \*